United States Patent [19]
Fortney et al.

[11] Patent Number: 6,017,531
[45] Date of Patent: Jan. 25, 2000

[54] HYDROPHILIC COMPOSITION CONTAINING PROTEASE PRODUCED BY VIBRIO

[75] Inventors: Donald Zane Fortney, Westminster; Donald Richard Durham, Gaithersburg, both of Md.; Kang Yang, Chalfont, Pa.

[73] Assignees: W. R. Grace & Co., New York, N.Y.; Conn. / Teva Pharmaceuticals USA, Inc., Kulpsville, Pa.

[21] Appl. No.: 08/867,331

[22] Filed: Jun. 2, 1997

[51] Int. Cl.⁷ .............................. C12N 9/50; C12N 9/52; A61K 38/48
[52] U.S. Cl. .................. 424/94.63; 435/219; 435/220; 435/909
[58] Field of Search .................. 424/94.63; 435/212, 435/219, 220, 909

[56] References Cited

U.S. PATENT DOCUMENTS

| | | | |
|---|---|---|---|
| 3,409,719 | 11/1968 | Noe et al. | 435/219 |
| 3,677,900 | 7/1972 | Merket | 435/219 |
| 4,276,281 | 6/1981 | Crikelair | 424/94.64 |
| 4,329,430 | 5/1982 | Klein et al. | 435/219 |
| 4,420,484 | 12/1983 | Gorman | 514/332 |
| 4,668,228 | 5/1987 | Bolton et al. | 604/307 |
| 4,865,983 | 9/1989 | Durham | 435/264 |
| 5,104,656 | 4/1992 | Seth | 424/401 |
| 5,145,681 | 9/1992 | Fortney et al. | 424/94.63 |
| 5,505,943 | 4/1996 | Fortney et al. | 424/94.63 |

FOREIGN PATENT DOCUMENTS 0418443  3/1991  European Pat. Off. .

OTHER PUBLICATIONS

Merkel et al., Journal of Bacteriology, vol. 87, pp. 1227–1233 (1964).
Eros, I., Szirovicza—Ferenczi, I.; Ugri–Hunyadvari, E., Pharm. Ind. 43(1) 90–3 (1981), title: Studies on emulsion–ointment bases containing softeram.
Prytz et al., Enzymalia, vol. 22; pp. 367–376 (1965).
Boxer et al., Geriatrics; pp. 75–86 (1969).
Silverstein et al., Surgical Forum, pp. 31–33 (1972).
Silverstein et al., Surgery, vol. 73, pp. 15–22 (1973).
Harris et al., Texas Rep. on Biology and Medicine, vol. 31, pp. 771–776 (1973).
Merkel et al., Applied Microbiology, vol. 29, pp. 145–151 (1975).
Pennisi et al., Burns, pp. 169–172 (1976).
Wilkes et al., Methods in Enzymology, vol. 33; pp. 404–415 (1976).
Coopwood, Southern Med. Journal, vol. 69; pp. 834–836 (1976).
Buckman et al., J. of Surg. Res., vol. 20; pp. 1–5 (1976).
Shakespeare et al., Burns, vol. 6; pp. 15–20 (1978).
Merkel et al., Biochemistry, vol. 17; pp. 2859–2863 (1978).
Dreisbach et al., Journ. of Bacteriology, vol. 135; pp. 521–527 (1978).
Levick et al., Burns, vol. 4, pp. 281–284 (1978).
Nierman, Drugs, vol. 15, pp. 226–230 (1978).
Falces, Western Journ. of Medicine, vol. 133; pp. 59–60 (1980).
Silverstein et al., Journ. of Burn Care Rehabilitation, p. 49 (1981).
Makepeace, Burns, vol. 9; pp. 153–157 (1982).
Ellis, Br. J. Surg, vol. 69, pp. 241–243 (1982).
Holtz, Fertil. and Steril., vol. 41, pp. 497–507 (1984).
Doody et al., Fertil. and Steril., vol. 51, pp. 509–512 (1989).

*Primary Examiner*—Dian C. Jacobson
*Attorney, Agent, or Firm*—Beverly J. Artale

[57] ABSTRACT

Hydrophillic compositions and methods of use are provided for debriding and wound healing applications. The compositions contain certain proteases produced by microorganisms of the genus Vibrio.

12 Claims, 1 Drawing Sheet

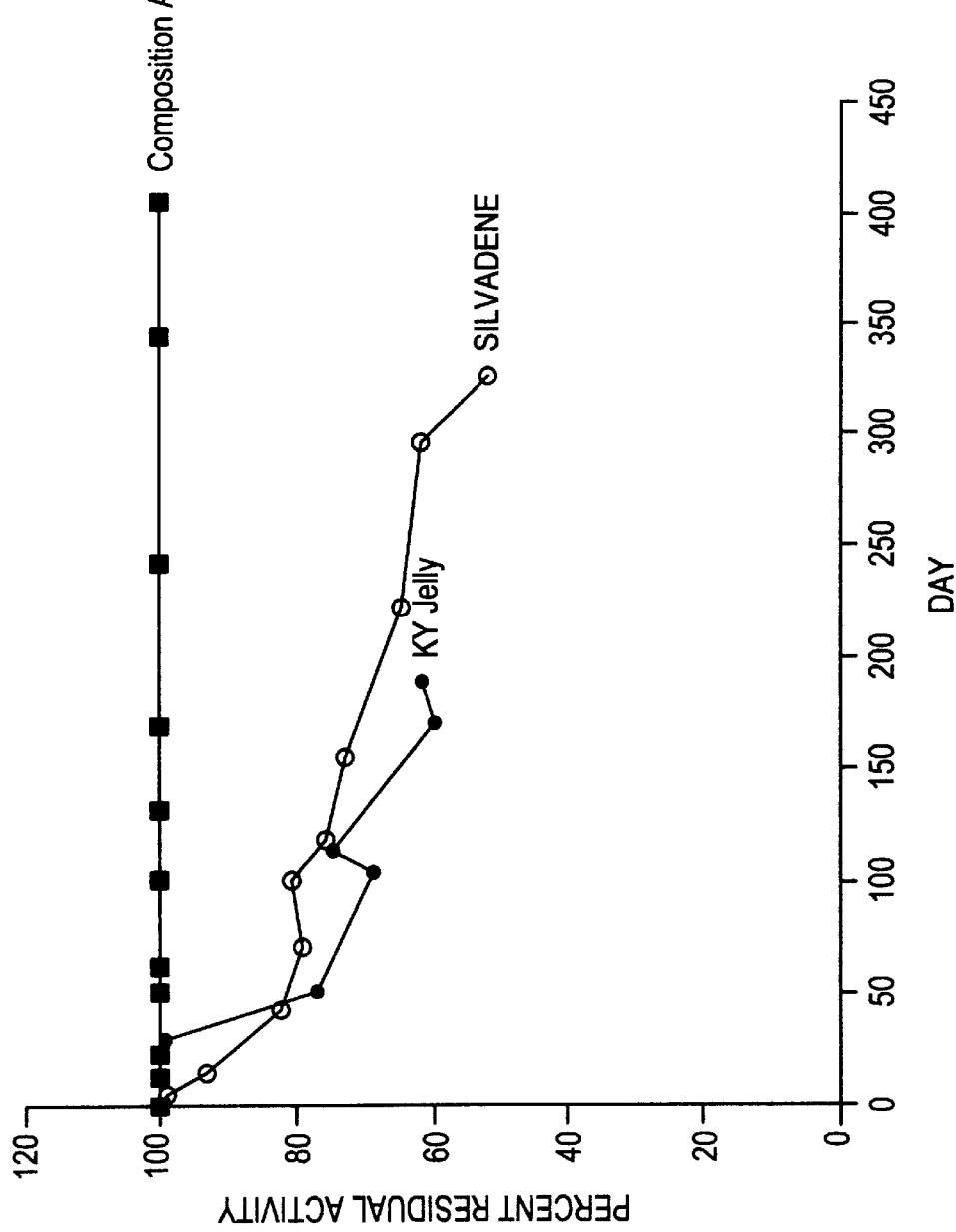

HYDROPHILIC COMPOSITION CONTAINING PROTEASE PRODUCED BY VIBRIO

TECHNICAL FIELD

The present invention relates to hydrophilic pharmaceutical compositions containing enzymes, particularly proteases. The composition is capable of maintaining enzyme activity at room temperature storage. More specifically, the present invention relates to hydrophilic compositions containing a protease produced by microorganisms of the genus Vibrio. The compositions are useful for debridement and/or wound healing. The present invention further relates to the usage of these pharmaceutical compositions for debridement and/or as wound healing agents.

BACKGROUND OF THE INVENTION

The healing of wounds is a complex process which is often further complicated by the presence of non-viable, necrotic tissue in the wound area. Debridement is the process of removing the non-viable tissue from a wound to prevent infection and facilitate healing.

Considerable efforts have been made to discover materials capable of distinguishing between viable and non-viable tissue. The discovery of materials which would digest devitalized tissue while not attacking viable tissue would make it possible to remove the devitalized tissue without surgery. It would be a beneficial therapeutic agent in virtually all disease processes or injuries where topically devitalized tissue needs to be removed from the wound area such as burns, cutaneous ulcers, pressure necroses, incisional, traumatic and pyogenic wounds, and ulcers secondary to peripheral vascular disease.

One area that has attracted considerable attention is the use of proteolytic enzymes and other chemicals to effect the early debridement of necrotic tissue from cutaneous ulcers and from burns. Such devitalized tissue is an excellent culture medium for microorganisms and moreover is the principal source of the septicemia which is the proximate cause of death, for example, in the majority of severely burned patients.

Devitalized tissue, which is commonly referred to as eschar, from cutaneous ulcers or burns is a complex mixture of dried blood, purulent exudates, and denatured proteins normally found in the epidermal and dermal skin layers. The denatured proteins found in eschar are primarily collagen, elastin, fibrin, hemoglobin, and other coagulated proteins.

Collagen comprises about 75% of the skin's dry weight and is the main constituent of the necrotic debris and of eschar. Strands of semi-viable, compromised collagen, whose protective mucopolysaccharide sheath has been damaged or destroyed, anchor the necrotic tissue to the wound surface. These strands must be fully eliminated in order for the necrotic material to be separated from its base. This complete debridement then permits development of granulation tissue during the healing process.

For a proteolytic enzyme to be suitable for use as a debriding agent, it is desirable for the protease to distinguish between viable and non-viable tissue; readily and thoroughly hydrolyze the wide variety of denatured proteins found in eschar; function at physiological pH and temperature; be compatible with adjunct therapies (e.g., cleansing agents, topical antibiotics); not interfere with normal wound healing; and remain stable in various formulations and at a wide range of temperatures. Furthermore, treatment of burn wounds with proteases should not complicate skin grafting. A number of proteolytic enzyme preparations have been used as debriding agents with varying degrees of success.

However, one problem associated therewith is that obtaining stable formulations of proteolytic enzymes is often problematic. A hydrophobic formulation is a water-in-oil emulsion, whereas a hydrophilic formulation is an oil-in-water emulsion. Most proteolytic enzymes are formulated into hydrophobic formulations and must be stored at refrigerated temperatures to stabilize the enzymes. For this reason, there are definite disadvantages of hydrophobic formulations. The disadvantages include the necessity to raise temperatures of the preparation before administration, reduced accessibility of the enzyme to the administration site, and difficulty in removing the formulation from the administration site by gentle cleansing procedures.

The composition of the invention overcomes the difficulties of the prior art by providing a hydrophilic formulation which stabilizes an enzyme, preferably a protease and more preferably a Vibrio protease and maintains the stability at ambient temperatures. Therefore, it is well suited for use as a therapeutic agent.

SUMMARY OF THE INVENTION

This invention provides hydrophilic pharmaceutical compositions capable of maintaining stable enzyme activity at room temperature. The compositions maintain enzyme activity at greater than 80% for at least 100 days at ambient temperatures. Glyceryl cocoate appears to impart enzyme stabilizing characteristics to the hydrophilic composition.

An especially preferred aspect of the invention is a composition which includes an extracellular neutral protease produced by *Vibrio proteolyticus* ATCC 53559. A particularly preferred procedure for preparation and method of use of this protease for debridement of necrotic tissue is described in commonly assigned U.S. Pat. No. 5,145,681, which is hereby incorporated by reference and relied on in its entirety. This embodiment of the invention is useful for treating wounds. Wound treatment includes debridement and wound healing.

Still another aspect of the invention is the usage of these stabilized neutral protease pharmaceutical compositions for debridement of necrotic tissue and as wound healing agents.

BRIEF DESCRIPTION OF THE FIGURE

FIG. 1 compares the shelf-life stability of various hydrophilic compositions containing vibriolysin.

DETAILED DESCRIPTION OF THE INVENTION

The proteases of this invention are characterized by a combination of properties which renders them ideal candidates for use in wound debridement and healing applications. By way of illustration and not limitation, these proteases:

i. hydrolyze components of necrotic tissue including denatured collagen, elastin and fibrin;
ii. do not substantially hydrolyze native tissue in vivo; and
iii. exhibit stable activity when stored at 25° C. in a topical formulation.

The proteases of the invention are capable of distinguishing between viable tissue and non-viable, necrotic tissue and are also active for sustained periods in formulations which are unacceptable to other proteases.

For the purposes of this application and the appended claims, the aforementioned properties of the proteases of this invention were determined as follows: Initial in vitro efficacy studies with the proteases of this invention, constituent proteins associated with eschar (e.g., denatured collagen, fibrin, denatured elastin) and native tissue were subjected to enzymatic hydrolysis. The proteases of this invention were shown to exhibit superior activity towards these substrates compared to proteases from Travase™. Furthermore, the proteases of this invention were shown to hydrolyze eschar from partial thickness wounds.

Preparation of the Protease

The proteases of this invention may be produced by fermentation of a suitable Vibrio species in a nutrient medium and then recovering the protease from the resulting broth. Fermentation is conducted aerobically in, for example, a casein hydrolysate, NZ-amine B, or soy flour nutrient medium containing inorganic salts such as sea salts, sodium sulfate, potassium dihydrogen phosphate, magnesium sulfate and certain trace elements at a pH of from about 7.6 to 8.6, preferably about pH 7.8, and at a temperature of from about 25° to 30° C., e.g., about 27° C., until the culture reaches early stationary phase growth.

The enzyme may thereafter be recovered from the fermentation broth by conventional procedures. Typically, the broth is first centrifuged or filtered to separate the cell portion and insoluble material. Thereafter, the supernatant fraction is concentrated by, e.g., ultrafiltration. The resulting ultrafiltrate may be used as is or may be precipitated with organic solvents such as acetone or inorganic salts such as ammonium sulfate, followed by centrifugation, ion-exchange chromatography or filtration in order to isolate an enzyme useful in debriding compositions. The protease is also stable when lyophilized. Other procedures known to those skilled in the art may also be used to cultivate the Vibrio microorganism and to recover the protease of this invention therefrom.

Useful microorganisms for use as a source of the instant proteases may comprise any suitable Vibrio, Aeromonas, Pseudomonas, Serratia or Bacillus or other marine microorganism species which secretes a protease having the above properties. A particularly preferred microorganism for this purpose is Vibrio proteolyticus (ATCC 53559). A viable culture of this microorganism has been irrevocably deposited with the American Type Culture Collection (ATCC), 10801 University Blvd., Manassas, Va. 20110-2209, with no restrictions as to availability, and W. R. Grace & Co.-Conn., the assignee hereof, assures permanent availability of the culture to the public through ATCC upon the grant hereof. The DNA sequence of the protease secreted by Vibrio proteolyticus (ATCC 53559), referred to herein as vibriolysin, is set forth in Sequence ID No. 1. While Vibrio proteolyticus (ATCC 53559) comprises the preferred protease source, other species of useful Vibrio microorganisms can readily be identified by those skilled in the art by screening the proteases produced, thereby using the procedures set forth above.

In addition to the direct cultivation of a Vibrio species, the proteases of this invention may also be prepared by the cultivation of recombinant host cells which have been transformed or transfected with a suitable expression vector with an insert containing the structural gene for the Vibrio-derived proteases of this invention or a fragment or mutant thereof which retains substantially the same protease activity as the native protease. Such procedures may be desirable, for example, in order to increase protease yields over that obtained with the wild type Vibrio microorganism or in order to produce improved mutant proteases.

Techniques for the cloning of proteases are well known to those skilled in the art of recombinant DNA technology, and any suitable cloning procedure may be employed for the preparation of the proteases of this invention. Such procedures are described, for example, in U.S. Pat. No. 4,468,464; European Published Patent Application No. 0,130,756; PCT Published Patent Application No. WO 87/04461; and Loffler, Food Technology, pages 64–70 (January 1986); the entirety of which are hereby incorporated by reference and relied on in their entirety.

A particularly preferred procedure for cloning the Vibrio proteases of this invention is described in commonly assigned U.S. Pat. No. 4,966,846, the entirety of which is hereby incorporated by reference and relied on in its entirety. According to the procedure of this patent, a gene library is first prepared, using the DNA of Vibrio source cells which have been determined by the assays described above to synthesize the proteases of this invention. Chromosomal DNA is extracted from the Vibrio source cells and digested with restriction enzymes by known procedures to give cleavage of the DNA into large fragments. Partial digestion with Sau3A is preferred, although other restriction enzymes (e.g., MboI, BamHI, etc.) may be used. The DNA fragments are then ligated into vectors suitable for allowing isolation of clones which express the protease enzyme. A preferred vector for this purpose is BamHI digested E. coli cosmid vector pHC79 (Bethesda Research Laboratories). The recombinant vectors (i.e., pHC79 cosmids containing DNA fragments from the protease-containing qenome) are then packaged into bacteriophage particles, preferably bacteriophage lambda, thereby producing a gene library in bacteriophage lambda particles. For production of a gene library in bacteriophage, a cosmid vector or lambda vector is used. In other cases, plasmid vectors may be used.

The resultant bacteriophage particles are then used to insert the gene library DNA fragments into suitable gram-negative host cells. Preferably, the recombinant bacteriophage particles are used to transect E. coli, such as, for example, E. coli strain HB101, although other strains of E. coli may be used if desired. Since E. coli strains do not naturally synthesize an extracellular neutral protease enzyme, the E. coli clones easily may be evaluated for the presence and expression of the protease gene by the assays described below.

It is known that colonies of Vibrio which synthesize protease enzyme will produce a zone of clearing on milk agar plates due to the proteolytic hydrolysis of the casein component of milk. Non-recombinant E. coli colonies do not secrete a protease naturally. Thus, E. coli clones of this invention which contain a functional protease gene are therefore readily identified by this assay. This milk-clearing assay is preferred for use with E. coli and other host strains which do not naturally produce an extracellular protease. Other gram-negative and gram-positive strains may be used as hosts.

Confirmation may be made by using other protease assays. For example, clones may be confirmed for expression of the protease enzyme by demonstrating that the fermentation broths of these clones are capable of hydrolyzing substrates such as Hide powder azure, azocoll or N-[3-(2-furyl)acryloyl]-alanyl-phenylalanamide (FAAPA). Alternatively, these assays may be used in the first instance to identify the protease gene-containing clones.

It is significant in two respects that expression of the neutral protease gene in E. coli and other "non-secreting" hosts (that is, hosts which do not naturally secrete a protease) can be detected as a zone of clearing on a milk agar plate. First, this is evidence that the active, functional enzyme is being synthesized by the gram-negative host.

Second, the extracellular presence of protease on the milk agar plates is evidence that the enzyme is being externalized in some manner, either by secretion or by cell lysis. Since *E. coli* and some other gram-negative bacteria normally do not secrete significant quantities of proteases into the media, this is important in terms of the ability to recover protease enzymes produced as a result of expression of Vibrio protease genes in these non-secreting hosts.

Sequence ID No. 1 contains the DNA sequence of the vibriolysin gene obtained from *Vibrio proteolyticus* ATCC 53559. This DNA sequence comprises a portion of a 6.7 kb Hind III fragment of the *Vibrio proteolyticus* gene described in U.S. Pat. No. 4,966,846, which encodes vibriolysin. An open reading frame exists from approximately base 249–2078, within which the DNA region encoding vibriolysin is found.

Also contemplated for use herein are mutants and hybrids of the foregoing proteases which substantially retain the preferred performance characteristics. As used herein, the term "mutant" refers to a protease in which a change is present in the amino acid sequence as compared with wild type or parent enzymes. This includes substitution, addition and deletion modifications. Also, this will include enzyme fragments or which comprise an internal deletion which possess protease activity. "Hybrid" refers to genetically engineered proteases which combine amino acid sequences from two or more parent enzymes and exhibit characteristics common to both.

Techniques for the preparation of mutant proteases are well known to those skilled in the art and include exposure of a microorganism to radiation or chemicals, site-directed mutagenesis, and cleavage with appropriate restriction enzymes. Mutagenesis by radiation or chemicals is essentially a random process and can require a tedious selection and screening to identify microorganisms which produce enzymes having the desired characteristics. Preferred mutant enzymes for the purposes of this invention are thus prepared by site directed mutagenesis. This procedure involves modification of the enzyme gene such that substitutions, deletions, and/or insertions of at least one amino acid at a predetermined site are produced in the protease enzyme. Techniques for site directed mutagenesis are well known to those skilled in the art and are described, for example, in the European Published Patent application No. 0 130,756 and PCT Published Patent application No. WO 87/04461, the entirety of which are hereby incorporated by reference and relied on in their entirety.

In one such procedure, known as cassette mutagenesis, silent restriction sites are introduced into the protease gene, closely flanking the target codon or codons. Duplex synthetic oligonucleotide cassettes are then ligated into the gap between the restriction sites. The cassettes are engineered to restore the coding sequence in the gap and to introduce an altered codon at the target codon.

The use of such procedures on the parent Vibrio proteases may be desirable in order to improve the properties of the wild type or parent protease. For example, the methionine, histidine, cysteine or tryptophan residues in or around the active site of the protease may be replaced in order to improve stability to chemical oxidation, as suggested in Estell et al., *J. Biological Chemistry*, Vol. 160, No. 11, pages 2518–2521 (1985).

Hybrids of the parent or wild type proteases may likewise be prepared by known protein engineering procedures analogous to the above-discussed cassette mutagenesis procedure by ligating a region of the gene of one parent enzyme (which need not be derived from Vibrio) into the gene of a second parent enzyme.

Clinical Properties of the Protease

The proteases of this invention are well suited for use in treating wounds and are particularly useful in wound debridement and wound healing applications. The properties can be demonstrated in a number of test situations, including animal and human clinical trials. One widely used assay is a partial thickness burn wound on pigs similar to that described by Mertz et al. (*Journal Surgical Research* (1990) 48:245–248). In this assay, the formulated protease can be compared to various controls to determine effectiveness.

For wound debridement, effectiveness is determined, among other indications, by absence, softening or dissolving of eschar; non-hydrolysis of viable tissue components; and/or non-irritation of the wound. In addition, debridement can be assessed histologically; wounds can be removed with a dermatome, fixed and embedded and sections cut and stained with, for example, Gomorils Trichrome stain. Analysis of such sections with a light microscope will reveal the extent of digestion of non-viable tissue. For topical wound healing, effectiveness is determined, among other indications by wound contracture, increased rate of healing and/or improved healing (i.e., maintain response to tactile stimulus, less scarring, improved neovascularization, etc.).

Formulation and Administration

Formulations of the debriding protease using available excipients and carriers are prepared according to standard methods known to those in the art. The protease can be formulated in ointments, lotions, gels, pastes, foams, aerosols, or immobilized on beads. The protease can also be immobilized in a wound dressing, tape or gauze. The enzyme formulations can be either hydrophilic or hydrophobic. Examples of hydrophobic bases include paraffin-mineral oil, and hydrophilic bases include petrolatum-propylene water bases. Hydrophilic formulations are preferred, particularly if the enzyme is stable in the formulation during storage at room temperature. Reasons for the preference include the convenience of not having to raise the temperature of the preparation before administering to the wound. More importantly, enzymes in a hydrophilic ointment should be more accessible for hydrolysis of necrotic tissue, and in contrast to a hydrophobic base, the ointment can be easily removed from the wound by washing with saline. Additional active ingredients, including antibiotics, humectants, deoxyribonucleases, fibronectin, growth factors such as fibroblast growth factor (FGF), epidermal growth factor (EGF) the transforming growth factors (TGF), insulin-like growth factors (IGF-1 and IGF-2), and/or platelet-derived growth factor (PDGF) and the like, can be included in the formulation, if desired.

Topical administration is most appropriate for wound debridement, although other routes of administration may be desirable under certain conditions. Standard topical formulations are employed using, for example, 0.01–10% protease by weight. Such formulations are usually repeatedly applied, e.g., about 1–6 times per day to the affected area. However, the number of applications, type of application, and concentration of the ointment or other formulation depends, of course, on the severity and type of the wound and nature of the subject.

Topical administration is also appropriate in order to stimulate vascularization and healing of traumatized tissue. Substrates include burns, bone fractures, surgical abrasions such as those of plastic surgery, cuts, lacerations, bed sores, slow-healing ulcers, tendinitis, bursitis, vaginitis, cervicitis, circumcisions, episiotomy, pilonidal cyst wounds, carbuncles, sunburn, frostbite.

Local, or possibly systemic, administration is appropriate for the prevention, or possibly treatment, of adhesions caused by surgical or other wounds. Local administration can be by injection, subcutaneous implant or slow release formulation implanted directly proximal the target. Implantation is directly practical especially under surgical conditions. Slow-release forms can be formulated in polymers as is well within the skill of the art. The concentration of protease in the formulation depends on a number of factors, including the severity of the condition and the rate of protease release from the polymer.

The following abbreviations have been used throughout in describing the invention:

$HBO_3$—boric acid
$CaCl_2$—calcium chloride
$CaSO_4$—calcium sulfate
cm—centimeter
$CUSO_4$—copper sulfate
° C.—degrees Centigrade
g—gram(s)
I.M.—intramuscular
kb—kilobase pair
$MgSO_4$—magnesium sulfate
$MnCl_2$—manganese chloride
mg—milligram(s)
ml—milliliter(s)
mm—millimeter(s)
mM—millimolar
mS—milli semen
nm—nanometer(s)
O.D.—optical density
%—percent
$K_2HPO_4$—potassium phosphate
NaOH—sodium hydroxide
$Na_2MoO_3$—sodium molybdate
$Na_2SO_4$—sodium sulfate
$H_2O$—water
w/v—weight to volume
$ZnSO_4$—zinc sulfate

EXAMPLES

The following examples serve to give specific illustration of the practice of this invention, but they are not intended in any way to act to limit the scope of the invention.

Example 1

Preparation of Vibriolysin

*V. proteolyticus* ATCC 53559 was cultured in a medium with the following composition (g or ml per liter): NZ-amine B, 40; $Na_2SO_4$, 25; dextrose, 10; $K_2HPO_4$, 4; $MgSO_4.7H_2O$, 0.4; Darastil-8270 (Dearborn) 0.1 ml and 6.1 ml of trace elements solution. The trace element solution comprises (grams per liter) the following: $ZnSO_4$. $7H_2O$, 18.29; $MnCl_2.4H_2O$, 18.86; $CaSO_4.2H_2O$, 0.91 g, $HBO_3$, 0.07; and $Na_2M_0O_4$. $2H_2O$, 0.04. Prior to sterilization, pH was adjusted to 7.0.

*V. proteolyticus* was cultured in either 1.5- or 10-liter fermentors. Fermentors containing the aforementioned medium were inoculated with 1% (v/v) culture obtained by growing *V. proteolyticus* in shake flasks containing medium of the same composition for 20 hours. The fermentations were performed at 28° C., 1,000–1,250 rpm and an aeration of 1.0 volume of air per volume of medium per minute. The pH of the fermentation was maintained at pH 7.8 by the automatic addition of an acid and base titrant.

Growth of *V. proteolyticus* was monitored by measuring optical density at 640 nm, and protease activity was monitored by quantifying the hydrolysis of azocasein. Azocasein hydrolysis is determined by incubating a sample of protease for ten minutes at 37° C. in 50 mM tris-HCl buffer (pH 7.4) containing 1.0 mg/ml of azocasein (sulfanilamide-azocasein, Sigma Corp., St. Louis, Mo.) with a final volume of 0.5 ml. At the end of this incubation period, 0.5 ml of 10% w/v trichloroacetic acid are added and immediately mixed and the resulting mixture is then stored on ice for 10 minutes. The mixture is then centrifuged and the optical density of the resulting supernatant is determined at 420 nm against a blank that contains either no enzyme or inactivated enzyme in the buffered azocasein solution. One unit of activity is defined as the amount of enzyme required to cause a change in absorbance of 2.5 at 420 nm. During the early stationary growth phase of the fermentation, the product protease reaches titers of approximately 85,200 to 127,800 azocasein units/liter as measured by the azocasein assay described earlier. The broth was harvested by centrifugation to separate the cell portion.

The supernatant fraction containing the proteolytic activity was concentrated using an Amicon SlOY10 spiral wound filter (Amicon Corp., Lexington, Massachusetts). The concentrate was diafiltered with 50 mM Tris buffer, pH 7.5, containing 1 mM $CaCl_2$ until the conductivity of the rententate was approximately 1 mS and the pH was neutral. This material was lyophilized and stored at −20° C. until used or formulated.

Example 2

Hydrophilic Cream Composition

A preferred hydrophilic cream composition (Composition A) was prepared as follows:

The cream contains the following ingredients at the indicated levels.

| Ingredient | Weight Percent |
| --- | --- |
| glyceryl cocoate | 34 |
| glyceryl trilaurate | 5 |
| glycerin | 13 |
| antimicrobial agent | 0.2 |
| phosphate buffer (pH 7.0) | 46 |
| Vibriolysin | 1.8 |

Glyceryl cocoate, glyceryl trilaurate and glycerin were mixed together and heated to 60° C. In a separate container, the anti-microbial, Cosmocil™ CQ (ICI Americas, Inc.) and phosphate buffer (0.3M $Na_2HPO_4$, pH 7.0) were combined and heated to 60° C. The buffer solution was then added to the glyceryl-containing solution and cooled with mixing to 40° C. The vibriolysin prepared as in Example 1 was then slowly added with mixing and allowed to cool to room temperature.

Example 3

Shelf-life Stability

Enzyme activity extracted from the hydrophilic composition, Composition A, prepared as described in Example 2, was monitored over time after storage at either 4° C. or 25° C. (ambient room temperature). One-tenth gram of composition was removed periodically, extracted with one ml of 100 mM TES (N-Tris [hydroxymethyl] methyl-2-amino ethanesulfonic acid) buffer, pH 7.5, containing 0.9% NaCl and 0.5 mM $CaCl_2$. The mixture was agitated thoroughly with a vortex, diluted 1:10 and residual proteolytic activity was determined by hydrolysis of azocasein as described in Example 1.

The residual proteolytic activity recovered from this composition is shown in FIG. 1 and is compared with vibriolysin containing hydrophilic compositions Silvadene™ (Hoechst Marion Roussel, Inc.) and KY Jelly™ (Johnson & Johnson). The stability of the enzyme in the invention composition is significantly better than prior art compositions.

Example 4

Releasibility of Protease from Compositions

One purported advantage of a hydrophilic composition is the accessibility of the therapeutic agent (e.g., protease) to the wound site. The releasibility of vibriolysin from various compositions was determined as follows: milk casein agar (1.5%) plates were prepared, and 6 mm circular wells were punched out of the agar. Each well was filled with either a vibriolysin composition or a vibriolysin buffer solution and the plates were incubated at 37° C. As the protease migrated from each well into the milk casein agar, it hydrolyzes the casein, leaving a zone of clearing of halo of hydrolysis around each well. Zones of hydrolysis were measured at a function of time and are shown below:

| Composition | Zones (mm) - of Hydrolysis at 7.5 h |
| --- | --- |
| Vibriolysin/buffer | 18.5 (100)[a] |
| Vibriolysin/Composition A | 16.2 (88) |
| Vibriolysin/Plastibase | 14.5 (78) |
| Vibriolysin/Silvadene | 17 (92) |

[a]Percent releasibility of enzyme.

These data indicate that vibriolysin is released more readily from the hydrophilic compositions; e.g. Composition A and Silvadene, than the hydrophobic composition Plastibase™ (Bristol-Myers Squibb Pharmaceuticals Ltd.).

Example 5

In vitro Activity of Composition

The vibriolysin-containing composition of Example 2 is useful for treatment of wounds. Native porcine skin is an excellent source of collagen (~70%), which is the principal component of necrotic tissue. To monitor debridement activity of the composition, a simple assay was devised that allows qualitative visualization of skin digestion. Briefly, the method consists of denaturing 3 $cm_2$ of Mediskin-I (porcine skin) (Bioplasty, Inc.) by boiling for 20 seconds. The denatured skin was blotted dry and mounted onto Petri dishes with surgical tape. The test composition (~1 g) was applied to the denatured skin, a solution of phosphate buffered saline (PBS) was added to the bottom of the dish to prevent desiccation of the skin. The dishes were covered and incubated at 37° C. After 6 to 24 hours incubation, the composition was removed from the skin using a gentle stream of phosphate buffered saline (PBS). Using this method, the vibriolysin composition was shown to completely hydrolyze the skin directly beneath the location where the enzyme composition was applied. It was further shown that this composition was more active than a vibriolysin/hydrophobic composition (e.g., Plastibase) and that the composition was superior to commercial products (e.g., Travase, Elase, Santyl, Granulex and Varidase) in hydrolyzing denatured pig skin collagen.

Example 6

In vivo Activity of the Composition

To assess the effectiveness of enzymatic digestion of eschar following either one or two treatments with the enzyme composition of Example 2, a third degree burn (full-thickness) injury was selected as the model. After appropriate anesthesia and shaving, three rows of steam burns were created on a pig. Six wounds were steamed for 30 sec, six wounds (40 sec), six wounds (50 sec). Wounds appeared white after injury with no apparent blood flow. The margins were red indicating a thin (2 mm) rim of second degree injury. The wounds were covered with an occlusive dressing (Op-Site). The pig was observed 24-hours later, and the dressing changed without anesthesia. At 48-hours post wounding, the pig was anesthetized. The wounds were washed with sterile saline. All wounds remained white with firm eschar. The formulations were applied and all wounds were covered with an occlusive bandage. The formulations were the Vibriolysin/Composition A of Example 2, an equivalent vehicle composition (without vibriolysin) and an untreated control. Twenty-four hours post treatment, the pig was anesthetized and the Op-Site was removed. The wounds were gently cleansed with sterile saline and gauze. Gross observations were recorded and photographs were made. A second application of formulations was applied and the pig was again wrapped in occlusive bandage. The percentage of eschar digestion is shown in Table I.

TABLE I

WOUND ESCHAR DIGESTION

|  | 30 Seconds | 40 Seconds | 50 Seconds |
| --- | --- | --- | --- |
| 24 Hours |  |  |  |
| Vibriolysin/Composition A | 50% | 50% | 50% |
| Vehicle | 0% | 0% | 0% |
| Untreated | 0% | 0% | 0% |
| 48 Hours |  |  |  |
| Vibriolysin/Composition A | 80% | 90% | 95% |
| Vehicle | 0% | 0% | 0% |
| Untreated | 0% | 0% | 0% |

After two treatments with the Vibriolysin/Composition A, 80–95% of the eschar was removed. The remaining base of the wounds were pink, and in several instances, subcutaneous blood vessels were observed through the fat. No spontaneous bleeding was noted. By comparison, the wounds that were untreated or treated with vehicle had firm eschar remaining.

Histological examination of harvested wounds corroborated visual, subjective assessments. Burn wounds were excised, fixed in 10% neutral buffered formalin for 48 hours and embedded in paraffin wax. Representative sections ($7\mu$) were stained with Gomori's Trichrome and photographed with an Olympus Vanox AH light microscope. Analysis of the sections of wounds treated with vibriolysin showed that hydrolysis proceeded downward throughout the non-viable epidermis and dermis to a level just above the subcutaneous fat. Sections of untreated wounds or wounds receiving vehicle revealed no hydrolysis.

We claim:

1. A hydrophilic pharmaceutical composition comprising a pharmaceutically effective amount of an enzyme and glyceryl cocoate in an amount effective to maintain enzyme activity at greater than 80 percent for at least 100 days at room temperature, wherein said enzyme is an extra cellular neutral protease produced by cultivation of *Vibrio proteolyticus* ATCC 53559.

2. The composition of claim 1, which is useful for debriding wounds.

3. The composition of claim 1, which is useful for promoting wound healing.

4. The composition of claim 1, wherein said protease is encoded by a DNA sequence having Sequence ID No. 1.

5. The composition of claim 1, which is useful for topical administration.

6. The composition of claim 1, which further comprises glycerin.

7. The composition of claim 1, which further comprises an anti-microbial agent.

8. The composition of claim 1, which further comprises about 0.5 to about 2.0% protease about 10.0 to about 70.0% glyceryl cocoate about 0 to about 30.0% glyceryl trilaurate about 0 to about 40.0% glycerin about 0.05 to about 0.5% antimicrobial about 30.0 to about 80.0% buffer.

9. A method of therapy which provides for the removal of necrotic and non-viable tissue from a subject in need of such treatment comprising administering a hydrophilic pharmaceutical composition according to claim 1.

10. The method of claim 9, wherein the therapy is effected for the treatment of a condition selected from burns, bone fractures, surgical abrasions, bed sores, slow healing ulcers, tendinitis, bursitis, vaginitis, cervicitis, circumcision, episiotomy, pilonidal cyst warts, carbuncles, sunburn and frostbite.

11. The method of claim 9, wherein the composition is topically applied.

12. The method of claim 11, wherein the composition is topically applied about 1 to 6 times daily.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 2000 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: CDS
       (B) LOCATION: 61..1890

(xi) SEQUENCE DESCRIPTION: SEQ ID NO:1:

```
TTTAATTTCT GATTTATCAG TAGTTAAACA ACGATTGAAA ATAATCTCCA GGATTGAGAA        60

ATG AAT AAA ACA CAA CGT CAC ATC AAC TGG CTG CTG GCT GTT AGC GCG        108
Met Asn Lys Thr Gln Arg His Ile Asn Trp Leu Leu Ala Val Ser Ala
 1               5                  10                  15

GCA ACT GCG CTA CCT GTC ACC GCT GCA GAA ATG ATC AAC GTA AAT GAT        156
Ala Thr Ala Leu Pro Val Thr Ala Ala Glu Met Ile Asn Val Asn Asp
                 20                  25                  30

GGC AGC CTG CTA AAC CAG GCT CTT AAA GCT CAG TCA CAG AGC GTT GCC        204
Gly Ser Leu Leu Asn Gln Ala Leu Lys Ala Gln Ser Gln Ser Val Ala
             35                  40                  45

CCG GTG GAA ACC GGA TTC AAA CAA ATG AAA CGA GTT GTT TTG CCA AAT        252
Pro Val Glu Thr Gly Phe Lys Gln Met Lys Arg Val Val Leu Pro Asn
 50                  55                  60

GGC AAA GTG AAA GTT CGT TAT CAA CAA ACT CAC CAC GGT CTA CCG GTT        300
Gly Lys Val Lys Val Arg Tyr Gln Gln Thr His His Gly Leu Pro Val
 65                  70                  75                  80

TTC AAC ACC TCG GTA GTG GCG ACT GAA TCG AAG TCT GGT AGT AGC GAA        348
Phe Asn Thr Ser Val Val Ala Thr Glu Ser Lys Ser Gly Ser Ser Glu
                 85                  90                  95

GTG TTC GGT GTG ATG GCT CAG GGT ATC GCA GAC GAC GTG TCT ACA CTG        396
Val Phe Gly Val Met Ala Gln Gly Ile Ala Asp Asp Val Ser Thr Leu
            100                 105                 110

ACG CCA TCC GTT GAG ATG AAG CAG GCC ATT TCA ATT GCT AAA TCG CGT        444
Thr Pro Ser Val Glu Met Lys Gln Ala Ile Ser Ile Ala Lys Ser Arg
            115                 120                 125

TTC CAA CAG CAA GAA AAA ATG GTT GCG GAA CCT GCA ACG GAA AAC GAA        492
Phe Gln Gln Gln Glu Lys Met Val Ala Glu Pro Ala Thr Glu Asn Glu
            130                 135                 140

AAA GCC GAG TTG ATG GTT CGT CTG GAC GAC AAC AAT CAA GCG CAA CTA        540
Lys Ala Glu Leu Met Val Arg Leu Asp Asp Asn Asn Gln Ala Gln Leu
145                 150                 155                 160

GTG TAT CTG GTT GAT TTC TTC GTT GCC GAG GAT CAC CCA GCG CGT CCT        588
Val Tyr Leu Val Asp Phe Phe Val Ala Glu Asp His Pro Ala Arg Pro
                165                 170                 175

TTC TTT TTC ATT GAT GCG CAA ACG GGT GAA GTA CTG CAA ACT TGG GAT        636
Phe Phe Phe Ile Asp Ala Gln Thr Gly Glu Val Leu Gln Thr Trp Asp
                180                 185                 190

GGT CTG AAC CAT GCA CAA GCT GAC GGT ACT GGC CCT GGC GGT AAC ACC        684
Gly Leu Asn His Ala Gln Ala Asp Gly Thr Gly Pro Gly Gly Asn Thr
            195                 200                 205

AAA ACA GGT CGT TAT GAA TAC GGT TCT GAC TTT CCT CCG TTT GTC ATC        732
Lys Thr Gly Arg Tyr Glu Tyr Gly Ser Asp Phe Pro Pro Phe Val Ile
```

-continued

```
            210                 215                 220
GAT AAA GTC GGC ACT AAG TGT TCA ATG AAC AAC AGC GCG GTA AGA ACG      780
Asp Lys Val Gly Thr Lys Cys Ser Met Asn Asn Ser Ala Val Arg Thr
225                 230                 235                 240

GTT GAC CTG AAC GGC TCA ACT TCA GGT AAC ACC ACT TAC AGC TAT ACC      828
Val Asp Leu Asn Gly Ser Thr Ser Gly Asn Thr Thr Tyr Ser Tyr Thr
                245                 250                 255

TGT AAC GAC TCA ACC AAC TAC AAC GAT TAC AAA GCC ATT AAC GGC GCG      876
Cys Asn Asp Ser Thr Asn Tyr Asn Asp Tyr Lys Ala Ile Asn Gly Ala
                    260                 265                 270

TAC TCG CCA CTG AAC GAT GCC CAC TAC TTC GGT AAA GTG GTT TTC GAT      924
Tyr Ser Pro Leu Asn Asp Ala His Tyr Phe Gly Lys Val Val Phe Asp
                275                 280                 285

ATG TAC AAA GAC TGG ATG AAC ACC ACA CCA CTG ACG TTC CAG CTG ACT      972
Met Tyr Lys Asp Trp Met Asn Thr Thr Pro Leu Thr Phe Gln Leu Thr
                290                 295                 300

ATG CGT GTT CAC TAT GGT AAC AAC TAC GAA AAC GCG TTC TGG AAT GGT     1020
Met Arg Val His Tyr Gly Asn Asn Tyr Glu Asn Ala Phe Trp Asn Gly
305                 310                 315                 320

TCA TCC ATG ACC TTC GGT GAT GGC TAC AGC ACC TTC TAC CCG CTG GTG     1068
Ser Ser Met Thr Phe Gly Asp Gly Tyr Ser Thr Phe Tyr Pro Leu Val
                325                 330                 335

GAT ATT AAC GTT AGT GCC CAC GAA GTG AGC CAC GGT TTC ACC GAA CAA     1116
Asp Ile Asn Val Ser Ala His Glu Val Ser His Gly Phe Thr Glu Gln
                340                 345                 350

AAC TCG GGT CTG GTG TAC GAG AAT ATG TCT GGT GGT ATG AAC GAA GCG     1164
Asn Ser Gly Leu Val Tyr Glu Asn Met Ser Gly Gly Met Asn Glu Ala
                355                 360                 365

TTC TCT GAT ATT GCA GGT GAA GCA GCA GAG TTC TAC ATG AAA GGC AGC     1212
Phe Ser Asp Ile Ala Gly Glu Ala Ala Glu Phe Tyr Met Lys Gly Ser
                370                 375                 380

GTT GAC TGG GTT GTC GGT GCG GAT ATC TTC AAA TCA TCC GGC GGT CTG     1260
Val Asp Trp Val Val Gly Ala Asp Ile Phe Lys Ser Ser Gly Gly Leu
385                 390                 395                 400

CGT TAC TTT GAT CAG CCT TCG CGT GAC GGC CGT TCT ATC GAC CAT GCG     1308
Arg Tyr Phe Asp Gln Pro Ser Arg Asp Gly Arg Ser Ile Asp His Ala
                405                 410                 415

TCT GAC TAC TAC AAT GGC CTG AAT GTT CAC TAC TCA AGT GGT GTA TTC     1356
Ser Asp Tyr Tyr Asn Gly Leu Asn Val His Tyr Ser Ser Gly Val Phe
                420                 425                 430

AAC CGT GCG TTC TAC CTG CTG GCT AAC AAA GCG GGT TGG GAT GTA CGC     1404
Asn Arg Ala Phe Tyr Leu Leu Ala Asn Lys Ala Gly Trp Asp Val Arg
                435                 440                 445

AAA GGC TTT GAA GTG TTT ACC CTG GCT AAC CAA TTG TAC TGG ACA GCG     1452
Lys Gly Phe Glu Val Phe Thr Leu Ala Asn Gln Leu Tyr Trp Thr Ala
                450                 455                 460

AAC AGC ACA TTT GAT GAA GGC GGT TGT GGT GTA GTG AAA GCT GCG AGC     1500
Asn Ser Thr Phe Asp Glu Gly Gly Cys Gly Val Val Lys Ala Ala Ser
465                 470                 475                 480

GAC ATG GGT TAC AGC GTT GCA GAC GTA GAA GAT GCG TTT AAC ACG GTA     1548
Asp Met Gly Tyr Ser Val Ala Asp Val Glu Asp Ala Phe Asn Thr Val
                485                 490                 495

GGC GTT AAC GCG TCT TGT GGT GCA ACT CCT CCT CCG TCT GGC GAT GTA     1596
Gly Val Asn Ala Ser Cys Gly Ala Thr Pro Pro Pro Ser Gly Asp Val
                500                 505                 510

CTG GAA ATC GGT AAA CCG CTG GCG AAC CTT TCA GGT AAC CGC AAT GAC     1644
Leu Glu Ile Gly Lys Pro Leu Ala Asn Leu Ser Gly Asn Arg Asn Asp
                515                 520                 525

ATG ACT TAC TAC ACG TTC ACA CCA AGC AGC TCA TCT AGC GTA GTG ATT     1692
Met Thr Tyr Tyr Thr Phe Thr Pro Ser Ser Ser Ser Ser Val Val Ile
```

```
                        530                     535                     540
AAG ATC ACT GGC GGT ACA GGT GAT GCA GAC CTT TAC GTG AAA GCG GGT                    1740
Lys Ile Thr Gly Gly Thr Gly Asp Ala Asp Leu Tyr Val Lys Ala Gly
545                         550                     555                     560

AGC AAG CCA ACC ACG ACT TCT TAC GAT TGC CGT CCA TAT AAG TAT GGT                    1788
Ser Lys Pro Thr Thr Thr Ser Tyr Asp Cys Arg Pro Tyr Lys Tyr Gly
                    565                     570                     575

AAC GAA GAG CAG TGT TCA ATT TCA GCG CAA GCG GGT ACT ACG TAT CAC                    1836
Asn Glu Glu Gln Cys Ser Ile Ser Ala Gln Ala Gly Thr Thr Tyr His
                580                     585                     590

GTT ATG CTG CGT GGT TAC AGC AAT TAC GCT GGT GTA ACT TTG CGT GCT                    1884
Val Met Leu Arg Gly Tyr Ser Asn Tyr Ala Gly Val Thr Leu Arg Ala
            595                     600                     605

GAC TAA ACTCAGAATG GAACCAGTGA AGGCGCACCT TAAGGTCGCC TTTTTTGTAT                     1940
Asp *
    610

CAGGCGATCT GTGTAAACGT GACCTGATCG AAGTGAGGAT TGGCCGCCAG CGCTTGCATG                  2000
```